(12) United States Patent
Palmateer et al.

(10) Patent No.: US 7,419,797 B2
(45) Date of Patent: Sep. 2, 2008

(54) RAPID COLIFORM DETECTION SYSTEM

(75) Inventors: Garry A. Palmateer, London (CA); Katarina D. M. Pintar, St. Agatha (CA); Michele I. Van Dyke, London (CA)

(73) Assignee: Conestoga - Rovers and Associates Limited, Waterloo (CA)

( * ) Notice: Subject to any disclaimer, the term of this patent is extended or adjusted under 35 U.S.C. 154(b) by 265 days.

(21) Appl. No.: 10/531,687

(22) PCT Filed: Oct. 17, 2002

(86) PCT No.: PCT/CA02/01557

§ 371 (c)(1),
(2), (4) Date: Nov. 2, 2005

(87) PCT Pub. No.: WO2004/035809

PCT Pub. Date: Apr. 29, 2004

(65) Prior Publication Data

US 2006/0134727 A1    Jun. 22, 2006

(51) Int. Cl.
*C12Q 1/04* (2006.01)
(52) U.S. Cl. ....................................................... 435/34
(58) Field of Classification Search ........................ None
See application file for complete search history.

(56) References Cited

U.S. PATENT DOCUMENTS

| | | | |
|---|---|---|---|
| 5,292,644 A | 3/1994 | Berg | |
| 5,510,243 A | 4/1996 | Boyd et al. | |
| 5,518,894 A | 5/1996 | Berg | |
| 5,861,270 A | 1/1999 | Nelis | |
| 5,972,641 A | 10/1999 | Ofjord et al. | |
| 6,063,590 A | 5/2000 | Brenner et al. | |

FOREIGN PATENT DOCUMENTS

| | | |
|---|---|---|
| DE | 196 08 320 | 8/1997 |
| EP | 0 841 403 | 5/1997 |
| WO | WO 94/20638 | 9/1994 |
| WO | WO 00/73412 | 12/2000 |

OTHER PUBLICATIONS

Nelis H J et al., "Comparison of Chemiluminogenic . . . ", Proceedings of the Water Quality Technology Conference, 1993, pp. 1663-1673.
Nelis H J et al., "Limitations of Highly Sensitive . . . ", Applied and Environmental Microbiology, Feb. 1997, p. 771-774.
Poucke S O et al., "A 210-min solid phase cytometry test . . . ", 2000, Journal of Applied Microbiology, 89 p. 390-396.
Tryland I et al., "Enzyme Characteristics of β-D- Galactosidase . . . ", Applied and Environmental Microbiology, Mar. 1998, p. 1018-1023.
Poucke S O et al., "Development of a Sensitive Chemiluminometric . . . ", Applied and Environmental Microbiology, Dec. 1995, p. 4505-4509.
George I et al., "Use of β-D- Galactosidase and β-D- Glucuronidase . . . ", Can. J. Microbiol. 47.:, 2001., p. 670-675.
Martin C S et al., "Dual Luminescence-Based Reported . . . ", Biotechniques, 1996, vol. 21, No. 3, p. 520-524.

*Primary Examiner*—Robert B. Mondesi
*Assistant Examiner*—Amanda P Wood
(74) *Attorney, Agent, or Firm*—Brunet and Co. Ltd.; Robert A. H. Brunet

(57) ABSTRACT

A system for rapidly determining the presence or quantity of coliform bacteria in a water sample using the enzymes β-D-galactosidase and β-D-glucuronidase. The system includes a first filter means for separating bacteria from the sample and a broth for culturing the bacteria including an inducing agent for inducing enzyme production. A second filter means is used to separate the cultured bacteria from the broth. A lysing agent is exposed to the bacteria on the second filter and incubated with a chemiluminogenic substrate of the enzyme to produce a chemiluminescent product. Light emission is initiated from the second filter means and the emitted light is detected or measured directly from the second filter means using a luminometer adapted to receive the second filter means. The system is especially effective at improving the sensitivity and specificity of the assay by increasing the signal received from encapsulated target organisms and reducing the interference from non-target organisms that may be present in the sample.

20 Claims, 4 Drawing Sheets

RAPID COLIFORM DETECTION SYSTEM

CROSS REFERENCE TO RELATED APPLICATIONS

This application is a PCT National Entry of International Application PCT/CA02/01557 filed on Oct. 17, 2002, which is hereby incorporated herein by reference.

1. Field of the Invention

The invention relates to a system for the rapid detection of coliform bacteria in water samples. Particularly, the invention provides a method and apparatus for rapidly determining the presence and/or quantity of coliform bacteria in a water sample for use, for example, in verifying the microbiological safety of the water for consumption.

2. Description of the Prior Art

To verify the microbiological safety of a water source for consumption, samples are normally tested in a laboratory for the presence of an indicator organism or group of organisms that signal the potential for pathogenic contamination of the sample. The coliform group of bacteria, consisting of *Klebsiella, Enterobacter, Citrobacter*, and *Escherichia coli*, is typically chosen as an indicator. Of these, *Escherichia coli* is of special significance, since it is associated with the intestinal tract of humans and warm-blooded animals and is a specific indicator of fecal contamination. As such, it can indicate the potential for contamination by pathogenic microorganisms. In water monitoring, total coliforms and *Escherichia coli* are the target organisms of any assay for determining the microbiological safety of the water source. The absence of coliform bacteria is taken as an indication of the safety of the water for consumption.

There are many different assays for coliform bacteria, including the presence/absence technique, the multiple tube fermentation technique and the membrane filtration technique. These assays have several disadvantages. A 24-hour incubation period is required for the detection of coliform bacteria, preventing results from being available until at least the next day, thereby creating the potential for public infection due to consumption of contaminated water in the intervening time period. Skilled personnel must be available to perform the assay on a nearly continuous basis and must return the following day to measure the assay result, even if that day falls on a weekend. A well-supplied lab is required and samples must be transported to the lab, increasing the elapsed time between taking the sample and performing the assay.

In order to overcome some of these disadvantages, more rapid coliform detection assays have been developed. These more rapid point-of-use assays are based on two target enzymes specific to the indicator bacteria. Coliform bacteria are identified based on production of the enzyme β-D-galactosidase, which is used in the metabolism of lactose. *Escherichia coli* are identified based on the production of the enzyme β-D-glucuronidase, which is used for the metabolism of glucuronide sugars. These target enzymes can be detected by the addition of a substrate that is cleaved in an enzyme catalyzed reaction that produces a detectable product. The substrate is typically either: chromogenic, detectable by colour change; fluorogenic, detectable by light emission when subjected to ultraviolet irradiation; or chemiluminogenic, detectable by visible light emission. If a quantity of the enzyme above a threshold value is detected, it is assumed that the target organisms containing the target enzyme are present and that the sample is not safe for consumption. The advantage of the assay is that the enzyme can be readily detected, minimizing the incubation time required to obtain a result.

Rapid enzymatic assays generally comprise the following steps. A sample of known volume is filtered through a microporous membrane filter using vacuum filtration, to separate and concentrate the bacterial cells from the original sample. The cells are then placed in contact with a bacterial growth medium for culturing in order to increase the quantity of cells, and hence the amount of enzyme available for detection. The cells are exposed to a lysing agent to rupture or permeabilize the cell membrane, and a substrate of the enzyme is added. Upon incubation, the substrate is hydrolyzed by the target enzyme to produce a detectable product. Depending on the type of substrate, the conditions required for detection of the product are then provided to determine the presence of the target enzyme.

In one embodiment of a rapid enzymatic assay, the filter and cells are placed in contact with a solid or semi-solid growth medium comprising growth nutrients, an inducing agent, a permeabilizing agent, and a substrate. The cells are simultaneously cultured to form microcolonies, permeabilized to increase exposure of the target enzyme to the substrate, and incubated to produce a detectable product. The conditions for detection of the product are then provided and the microcolonies are enumerated; for example, when a fluorogenic substrate is used, ultraviolet light is shone on the filter to initiate light emission from the microcolonies for optical detection. This is generally referred to as a single stage enzymatic assay, since cell culturing and enzyme incubation are combined. An example of a single stage enzymatic assay is provided by Berg in U.S. Pat. No. 5,292,644.

A disadvantage of single stage enzymatic assays is that the permeabilizing agent is present during cell culturing. Since cell permeabilization is bactericidal in nature, the permeabilizing agent impedes the replication of cells and the formation of microcolonies, limiting the sensitivity of the assay. In order to overcome this limitation, two-stage assays have been developed. In the two-stage assay, the permeabilizing agent is left out of the growth medium during culturing, or pre-incubation. After microcolony formation, a permeabilizing agent is added, and the permeabilized or lysed cells are incubated in the presence of the substrate. Light emission is then initiated and microcolonies are counted. An example of a two-stage enzymatic assay is provided by Nelis in U.S. Pat. No. 5,861, 270.

The foregoing assays are not directed specifically to drinking water. During drinking water treatment, bacterial cells are exposed to oxidizing agents, such as chlorine, chloramine, chlorine dioxide, and/or ozone. It is understood that this treatment stresses the cells, reducing their ability to replicate on solid growth media and to form microcolonies (Rompre, A., Servais, P., Baudart, J., de-Roubin, M., Laurent, P. 2002. Detection and enumeration of coliforms in drinking water: current methods and emerging approaches. *J. Microbiol. Methods.* 49:31-54; Clark, J. A. 1990. The presence-absence test for monitoring drinking water quality. In Drinking Water Microbiology (G. A. McFeters, Ed.), Springer Verlag, p. 399-411.). To increase the recovery and detection of cells, especially when analyzing a drinking water sample, it is preferable to culture in a liquid growth medium.

Nelis et al. in Proceedings of the Water Quality Technology Conference (AWWA), Miami, Fla., Nov. 7-11, 1993, pp. 1663-1673, disclosed a two-stage enzymatic assay using a liquid growth medium, without the formation of microcolonies. Samples were filtered and both the filter and cells were placed in the liquid growth medium and cultured in a pre-incubation step. The lysing agent and a chemiluminescent substrate were then added to the liquid growth medium and another incubation step was conducted. A light signal was obtained from the liquid growth medium using a luminometer.

However, in U.S. Pat. No. 5,861,270, Nelis discloses that non-target bacteria, such as *Aeromonas* spp., that have the target enzyme often interfere with the measurement and that when measurements are taken from the liquid growth medium, there is potential for a false-positive result to arise due to this interference. Similarly, Nelis et al. in "Limitations of Highly Sensitive Enzymatic Presence-Absence Tests for Detection of Waterborne Coliforms and *Escherichia coli*", (Applied and Environmental Microbiology 63(2):771-774, 1997) found that for the surface water and drinking water samples analyzed, the ratio of the signal obtained from target organisms to the noise generated by non-target organisms was insufficient to reliably detect the presence of target organisms and prevent false-positive results when the light signal was obtained from a liquid growth medium using a luminometer.

The prior art methods typically require the formation of microcolonies on the filter. These microcolonies must be counted to determine the microbiological safety of the water supply, which is a time consuming process. To automate the counting of colonies on the filter, a complicated and expensive apparatus is required that uses a CCD camera connected to a computer for image processing; for example, a suitable commercially available apparatus is the ChemScan RDI™ (Chemunex, Paris, France). Like a microscope, the CCD camera has a defined focal length and cannot readily discern microcolonies at a range of depths within the micropores of the filter. Progressive scans are typically taken at a plurality of focal lengths in order to count all microcolonies present on the filter. The formation of microcolonies therefore creates a limitation in the automation of the prior art assays.

The present invention seeks to overcome one or more of the aforementioned disadvantages of limited sensitivity, insufficient signal-to-noise ratio, and the need to count microcolonies in a rapid yet low-cost enzymatic assay for assessing the microbiological safety of a water supply.

SUMMARY OF THE INVENTION

According to an aspect of the invention, there is provided a method for determining the presence of coliform bacteria in a water sample comprising the steps of: separating the bacteria from the sample using a first filter means; culturing the bacteria in a broth comprising nutrients for supporting growth of the bacteria and an inducing agent for inducing enzyme production in the bacteria; separating the bacteria from the broth using a second filter means; exposing the bacteria to a lysing agent; incubating a chemiluminogenic substrate of the enzyme with the enzyme to cause cleavage of the substrate, thereby producing a luminescent product; initiating light emission by exposing the luminescent product to an enhancing agent; and, detecting the light emission to thereby determine the presence of the bacteria in the sample. In a preferred embodiment of the invention, the water sample is drinking water. In another embodiment, the bacteria are separated from the broth before being exposed to the lysing agent. In yet another embodiment, the bacteria are on the second filter means during exposure to the lysing agent. In yet another embodiment, the light emission is detected by a luminometer. In yet another embodiment, the second filter means is placed within the luminometer during detection of the light emission.

According to another aspect of the invention, there is provided a method for determining the quantity of coliform bacteria in a water sample comprising the steps of: separating the bacteria from the sample using a first filter means; culturing the bacteria in a broth comprising nutrients for supporting growth of the bacteria and an inducing agent for inducing enzyme production in the bacteria; separating the bacteria from the broth using a second filter means; exposing the bacteria to a lysing agent; incubating a chemiluminogenic substrate of the enzyme with the enzyme to cause cleavage of the substrate, thereby producing a luminescent product; initiating light emission by exposing the luminescent product to an enhancing agent; and, measuring the light emission to obtain a light measurement corresponding to the quantity of the enzyme to thereby determine the quantity of the bacteria in the sample. In a preferred embodiment of the invention, the water sample is drinking water. In another embodiment, the bacteria are separated from the broth before being exposed to the lysing agent. In yet another embodiment, the bacteria are on the second filter means during exposure to the lysing agent. In yet another embodiment, the light emission is detected by a luminometer. In yet another embodiment, the second filter means is placed within the luminometer during detection of the light emission.

According to yet another aspect of the invention, there is provided a kit for determining the presence or quantity of coliform bacteria in a water sample comprising: a first filter means for separating the bacteria from the sample; a broth for culturing the bacteria comprising nutrients for supporting growth of the bacteria and an inducing agent for inducing enzyme production in the bacteria; a second filter means for separating the bacteria from the broth; a lysing agent for exposure to the bacteria; a chemiluminogenic substrate of the enzyme for incubation with the enzyme to cause cleavage of the substrate, thereby producing a luminescent product; an enhancing agent for initiating light emission upon exposure to the luminescent product; wherein said kit is adaptable for use in detecting or measuring the light emission from the luminescent product. In a preferred embodiment of the invention, the water sample is drinking water. In another embodiment, the bacteria are separated from the broth before being exposed to the lysing agent. In yet another embodiment, the bacteria are on the second filter means during exposure to the lysing agent. In yet another embodiment, the kit includes a luminometer for use in detecting or measuring the light emission. In yet another embodiment, the light emission is detected or measured by a luminometer. In yet another embodiment, the second filter means is placed within the luminometer during detection of the light emission.

According to yet another aspect of the invention, there is provided a method for determining the presence of coliform bacteria in a drinking water sample comprising the steps of: separating the bacteria from the sample using a first filter means; culturing the bacteria at a temperature of about 22 to 45° C. for about 2 to 10 hours in a broth comprising nutrients for supporting growth of the bacteria and an inducing agent comprising isopropyl-β-D-thiogalactopyranoside (IPTG) or methyl-β-D-glucuronide (Met-Glu) for inducing production of an enzyme in said bacteria; separating the bacteria from the broth using a second filter means; followed by, exposing the bacteria on the second filter means to a lysing agent comprising polymyxin-B; incubating a chemiluminogenic substrate of the enzyme comprising 1,2-dioxetane with the enzyme to cause cleavage of the substrate, thereby producing a luminescent product on the second filter means; initiating light emission by exposing the luminescent product to an enhancing agent comprising quaternary ammonium homopolymer; and, detecting or measuring the light emission using a luminometer by placing the second filter means with the luminescent product within the luminometer to thereby determine the presence or quantity of the bacteria in the sample.

A water sample is taken from a water source. The water source may be a natural water source, for example a lake or river, or a drinking water source, for example a groundwater well, a conventional water treatment plant, or tap water. The water sample is of known volume and bacterial cells present are separated from the sample using a first filter. The separation method may include gravity assisted filtration, pressurized filtration, or preferably vacuum filtration. A relatively large volume sample, typically one liter, is taken to increase the number of bacteria present on the filter, improving the likelihood of detection. Since it is often desirable to detect two types of target organisms, for example total coliforms and *Escherichia coli*, two or more samples of water may be taken and filtered at the same time in order to conduct the assays in parallel, reducing the overall amount of time required to obtain results. Alternatively, a single sample may be split into two aliquots. The first filter is typically a microporous membrane filter with a nominal pore size of about 0.22-0.45 μm and diameter of about 25-47 mm. The filter may be made of any suitable material, such as a ceramic, cellulose ester, polycarbonate, nylon, or a hydrophobic material, for example, polytetrafluoroethylene (PTFE) or polyvinylidene fluoride (PVDF). Preferably, the filters are made of cellulose ester or polycarbonate. Experimentally, polycarbonate filters produced the lowest background noise levels. The hydrophobic filters are generally more expensive than the other types and experimentally no significant increase in light emission was observed using the hydrophobic material.

In order to increase the amount of enzyme available for detection, the collected cells are transferred to a broth for culturing. A broth is preferred over a nutrient agar to rapidly achieve a high degree of cellular growth, especially when culturing the stressed bacterial cells present in drinking water. The membrane filter may be present with the bacteria in the broth without any observed detrimental effect on the quantity of cells produced. A suitable broth contains nutrients to promote bacterial growth and may contain additional substances to maintain the osmotic balance, increase buffering capacity, indicate pH changes, and selectively inhibit the growth of non-target organisms. Additionally, a suitable broth contains an inducing agent to induce the production of the desired enzyme in the cultured bacteria.

Although any suitable broth may be used, an example of a preferred broth comprises (per liter): 3.0 g beef extract; 5.0 g pancreatic digest of gelatin; 7.5 g lactose; 10.0 g pancreatic digest of casein; 1.375 g dipotassium phosphate; 1.375 g monopotassium phosphate; 2.5 g sodium chloride; and, optionally, 0.05 g sodium lauryl sulfate. The sodium chloride is provided to maintain the osmotic balance of the broth and the sodium lauryl sulfate is an inhibiting agent optionally added to suppress the growth of non-target organisms. The antibiotic cefsulodin is another example of an inhibiting agent that may be used. To inhibit the growth of *Aeromonas*, cefsulodin in the amount of about 12 μg/mL of media is recommended. The final pH of the broth is typically 6.8; optionally, 8.5 mg of bromcresol purple may be added as a pH indicator. Of note is the absence of bile salts from the broth, since they have a detrimental effect on the growth of certain target organisms of the coliform group.

To this broth is added an agent for inducing enzyme production in the cultured bacteria. For example, to induce the production of β-D-galactosidase, an inducing agent such as isopropyl-β-D-thiogalactopyranoside (IPTG), lactose, or a combination thereof may be used. To induce the production of β-D-glucuronidase, an inducing agent such as isopropyl-β-D-thioglucuronide or preferably methyl-β-D-glucuronide (Met-Glu) may be used. Culturing in this type of broth increases both the number of bacterial cells and the quantity of enzyme available for detection, especially when starting from stressed bacterial cells of the type commonly found in drinking water samples.

To culture the bacteria, the broth containing cells is incubated at a temperature of about 22 to 45° C. for about 2 to 10 hours. When the assays are conducted in parallel, the total coliform assay may be completed before the *Escherichia coli* assay; if a negative result is obtained for total coliforms, a corresponding negative result may be inferred for *Escherichia coli*, eliminating the need to complete the parallel assay. For the growth of coliforms, incubation is at about 35° C. for about 5 hours. For the growth of *Escherichia coli*, incubation is at about 44.5° C. for about 9 hours. These culturing conditions were found optimal for achieving the desired assay sensitivity.

Following culturing, the bacterial cells are separated from the broth and collected on a second filter. Any of the separation methods previously discussed may be used. The preferred separation method is vacuum filtration and the second filter is typically a microporous membrane filter similar to the first filter. The second filter is preferably about 25-47 mm in diameter with a nominal pore size of about 0.22-0.45 μm and made of a cellulose ester material.

The collected cells are then exposed to a lysing agent that disrupts the integrity of the cell membrane. Preferably, the lysing agent is added directly to the second filter after filtration of the broth so that the bacteria are present on the second filter during exposure to the lysing agent. Lysing the cell membrane allows transfer of enzymes and other molecules, such as chemiluminogenic substrates, across the membrane, promoting mixing and reaction of the substrate with the enzyme. Cell lysis also prevents the cells from reproducing and forming microcolonies on the filter. The lysing agent may be toluene, mechanical beads, freezing, a change of pressure, lysozyme, various detergents, or a combination of detergent and the antibiotic polymyxin-B. The preferred lysing agent comprises: a buffer, for example 100 mM potassium dihydrogen phosphate (pH 7.8); a surfactant, for example, 0.2% octylphenoxypolyethoxyethanol (nonionic surfactant); and/or an antibiotic, for example, 0.01 g/L polymyxin-B. Octylphenoxypolyethoxyethanol nonionic surfactant is also known as alkylphenolhydroxypolyoxyethylene, alkylaryl polyether alcohol, or octyl phenol ethoxylate and sold commercially under the name Triton-X-100® (Mallinckrodt Baker, Inc., Phillipsburg, N.J.). Preferably about 500 μL of the lysing agent, including 0.01 g/L of polymyxin-B, is added directly to the filter.

A substrate is selected based on the target enzyme. The substrate may be added directly to the lysed cells on the second filter. The preferred chemiluminescent substrates are 1,2-dioxetane derivatives. Dioxetanes are four-membered cyclic peroxides that may be coupled to R-groups selected by their affinity for the target enzyme. It is desirable to choose a substrate with prolonged light emission kinetics in order to increase the time available for detection of a light signal. For example, 3-chloro-5-(4-methoxyspiro{1,2-dioxetane-3,2'-(5'-chloro)-tricyclo-[3.3.3.3$^{3,7}$]decan}-4-yl)phenyl β-D-galactopyranoside, commercially available under the name Galacton-Plus™ (Applied Biosystems, Foster City, Calif.), is a substrate that may preferably be used for the enzyme β-D-galactosidase. For another example, sodium 3-(4-methoxyspiro{1,2-dioxetane-3-,2'-(5'-chloro)-tricyclo-[3.3.1.1$^{3,7}$] decan}-4-yl)phenyl β-D-glucuronate, commercially available under the name Glucuron™ (Applied Biosystems, Foster City, Calif.), is a substrate that may preferably be used for the enzyme β-D-glucuronidase. The 1,2-dioxetane emits visible light following cleavage of the R-group by the enzyme. A substrate volume of about 50-400 μL, preferably about 200 μL, is added. The lysed cells and substrate, preferably both on the second filter, are then incubated in order to promote a cleavage reaction of the substrate by the enzyme, thereby creating the luminescent product. Incubation is preferably at about 37° C. for about 30 minutes.

Under ideal conditions, light emission builds slowly and reaches a maximum after a specific incubation time. However, emission of light from the cleaved dioxetane product is influenced by pH. Under the neutral pH conditions normally encountered during incubation the dioxetane becomes protonated, preventing production of a detectable light signal. Water molecules contribute to this quenching of the light signal due to enhanced proton transfer. A stable intermediate thus accumulates during the incubation period that will only emit light once the pH is increased. One means of initiating light emission from accumulated intermediates is through the addition of an enhancing agent. The enhancing agent increases the pH, thereby excluding water from the cleavage site of the dioxetane and preventing immediate quenching of the light signal due to water molecule induced protonation. Some enhancing agents of this type comprise quaternary ammonium homopolymers, such as poly(benzyltributyl)ammonium chloride. Examples of these enhancing agents are commercially available under the names Emerald II™ (Tropix, Applied Biosystems, Foster City, Calif.) for β-D-galactosidase and Sapphire II™ (Tropix, Applied Biosystems, Foster City, Calif.) for β-D-glucuronidase. A quantity of about 50-400 μL, preferably about 200 μL, is added. Preferably, the luminescent product is on the second filter means and the enhancing agent is added to the second filter means.

The light emitted is detected or measured using a luminometer. A luminometer typically comprises a sample receiving port in optical communication with a photomultiplier tube or photodiode for detecting a light signal emitted from the sample. The sample receiving port may be designed to accommodate a liquid sample contained within an optically transparent container, such as a cuvette, or a sample with a substantially flat light-emitting surface, such as a membrane filter. It is preferable to use a simple and inexpensive luminometer to minimize the potential for operator error and reduce the cost of the assay. For example, a Berthold FB12 luminometer may be used (Berthold Technologies USA LLC, Oak Ridge, Tenn.) that is capable of detecting or measuring a light signal emitted from either a cuvette or a flat membrane filter. Preferably, the luminescent product is on the second filter during detection of the light emission. Placing the second filter flat within the luminometer permits detection or measurement of a signal directly from the filter in order to recover light emitted by substantially all of the luminescent product, including luminescent product on the filter that may be associated with cells trapped within the pores of the filter. Obtaining a signal directly from the filter therefore improves the sensitivity of the assay.

To determine the presence or quantity of the target organism, observation of microcolonies is not required, since there are no microcolonies present on the filter. Instead, the overall light signal obtained from the filter with the luminometer is used. A signal to noise ratio in excess of 1, preferably in excess of 2, generally indicates the presence of the target organism and that the original water sample is unsafe for consumption. To semi-quantitatively determine the quantity of target organisms present, the measured light signal is compared with a calibration curve. The light signal can be correlated with the quantity of target enzyme or target organisms; for example, the light signal exhibits a sigmoidal response to an increasing number of target organisms. A log transformation of the sigmoidal response may be used to linearize the data for creation of a calibration curve. A calibration curve may be prepared using known quantities of enzyme or pure culture organisms. The calibration curve may then be used to determine the quantity of target organisms present in a water sample based on the measured light signal.

In order to reliably determine the microbiological safety of a water supply, the assay must have sufficient sensitivity to detect target organisms and sufficient specificity to determine target organisms from non-target organisms. The present invention has the advantages of enhanced sensitivity and specificity, as compared with previous assays.

The sensitivity of the assay, or minimum detection limit, is the smallest number of organisms that may be detected. In the present invention, sensitivity is enhanced by providing both an increased quantity of enzyme and improved detection of the enzyme as compared with prior art assays. By culturing in a liquid broth, the stressed organisms present in drinking water are able to recover and replicate more readily, ultimately increasing the availability of enzyme for detection. By adding a second filtration step after broth culturing, cell lysis can be conducted directly on the filter, which is more effective at lysing encapsulated organisms such as *Klebsiella*. The addition of a second filtration step also means that a signal may be obtained directly from the filter using the preferred luminometer, which allows all of the target organisms on the filter to contribute to the total available signal. Also, by performing cell lysis, substrate incubation and signal detection directly on the second filter, enzyme that is trapped within incompletely lyzed cells can still be measured. Some coliform bacteria, for example *Klebsiella*, can produce high amounts of capsular material that can interfere with the lysis procedure. In this method, encapsulated organisms that are partially lyzed remain on the filter, and substrate enzyme interactions within the cell will be measured. The degree of lysis of encapsulated organisms may also be increased by adding the lysing agent directly to the filter. All assays that measure light emission will have a certain level of non-specific background noise; the reagents and luminometer used in this assay result in a reduced background noise level, providing a lower signal detection limit. All of these factors increase the quantity of available enzyme and improve the sensitivity of the assay as compared with prior art methods.

The specificity of the assay depends on the detection of target bacteria only, with no interfering signal from non-target organisms or non-specific background noise. Non-target organisms generally produce a much lower amount of target enzyme per cell. In addition, the growth of non-target bacteria can be inhibited by using culture broth containing antibiotic agents, such as cefsulodin. Both of these factors can increase the specificity of the assay, so that only target organisms are detected.

The assay may be performed manually or automatically. For manual use, a kit may be assembled comprising the required reagents in pre-determined proportions to facilitate the assay. Filters, glassware, and a luminometer may optionally be provided as part of the kit. Calibration standards may also be included in the kit. To automate the assay, a device may be used that performs several or all of the method steps.

Further features of the invention will be described or will become apparent in the course of the following detailed description of examples. However, this description is not intended to limit the scope of the invention.

BRIEF DESCRIPTION OF THE DRAWINGS

In order that the invention may be more clearly understood, a preferred embodiment thereof will now be described in detail by way of example, with reference to the accompanying drawings, in which.

EXAMPLES

Example 1

Comparison of a light signal in relative light units (RLU) for coliforms obtained by taking measurements from a liquid sample in a microtube and taking measurements directly from a flat filter.

Figure 1:
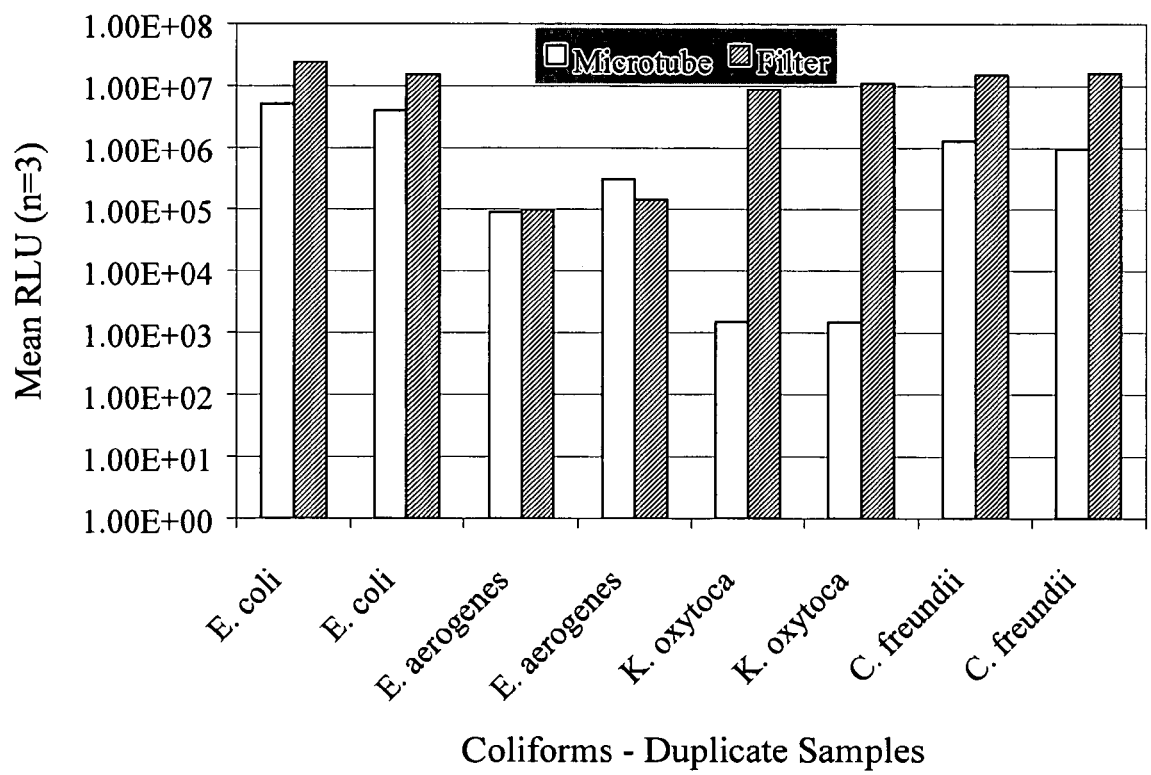
FIG. 1 shows a comparison of light measurements obtained from a microtube and directly from the filter for coliform bacteria.

Organisms from each genus of the coliform group of bacteria were cultured and duplicate samples were taken. Each sample was divided into two aliquots. For each aliquot, lysis was performed on the filter after the second filtration step in accordance with the assay of the present invention. For one of the aliquots from each sample, the filter containing cells was rolled up and placed in a 1.5 mL microtube for insertion into a conventional luminometer. For the other aliquot, the filter was placed lying flat and facing up on a filter holder for insertion into a Berthold FB-12 luminometer. Light measurements were taken from both aliquots and the results were plotted in FIG. 1.

A paired t-test (df=7) supports the observation that there is a statistically significant difference between the light signal obtained from the microtube vs. the signal obtained directly from the filter, with a p-value of 0.005. A stronger signal was generally obtained by taking light readings directly from the filter. This was especially true for *Klebsiella*, where the Mean RLU increased by approximately 4 orders of magnitude when measurements were taken directly from the filter. This increases the contribution to the total light signal by the target organism *Klebsiella* when present in a real water sample, increasing the overall sensitivity of the assay.

Example 2

Comparison of signal to noise ratio for varying pre-enrichment levels of *Aeromonas* with and without the antibiotic cefsulodin.

A pure culture of *Aeromonas* was prepared and diluted to obtain a number of samples with pre-enrichment concentrations of *Aeromonas* up to about 105,000 colony forming units (CFU) per mL of solution. Each sample was divided into aliquots. To one of the aliquots the antibiotic cefsulodin was added at a concentration of 12 µg/mL. The assay of the present invention was performed and the results are shown in FIG. 2.

Figure 2:
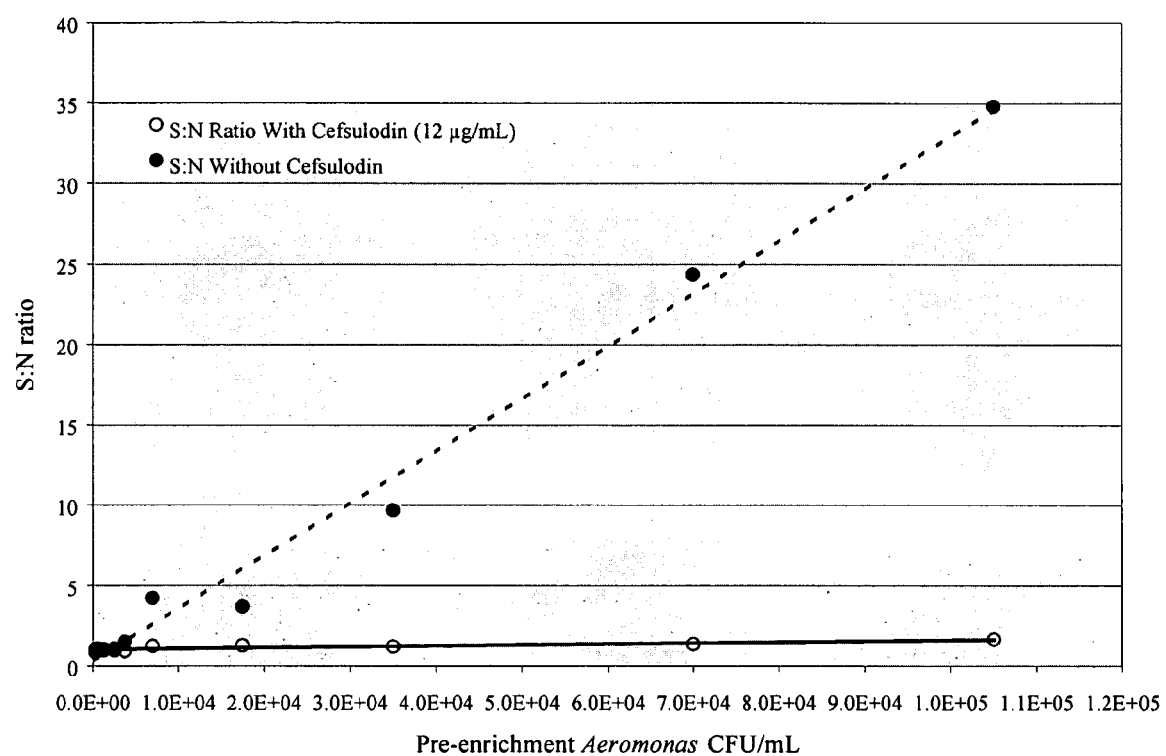
FIG. 2 shows the effect of cefsulodin on the light signal obtained from samples containing *Aeromonas*.

The S:N ratio shown in FIG. 2 indicates the signal obtained from *Aeromonas* only, which would normally be attributed to false-positive results when target organisms are not present but *Aeromonas* is present. Without the addition of cefsulodin, increasing concentrations of *Aeromonas* lead to an increasing S:N ratio, which could result in false-positive results. Samples containing cefsulodin showed essentially no change in S:N ratio with increasing *Aeromonas* concentration, indicating that cefsulodin effectively inhibits the false-positive contribution of *Aeromonas* to the light signal obtained from a real water sample.

Example 3

Comparison of S/N ratio for false-positive non-target organisms to target organisms.

Figure 3:
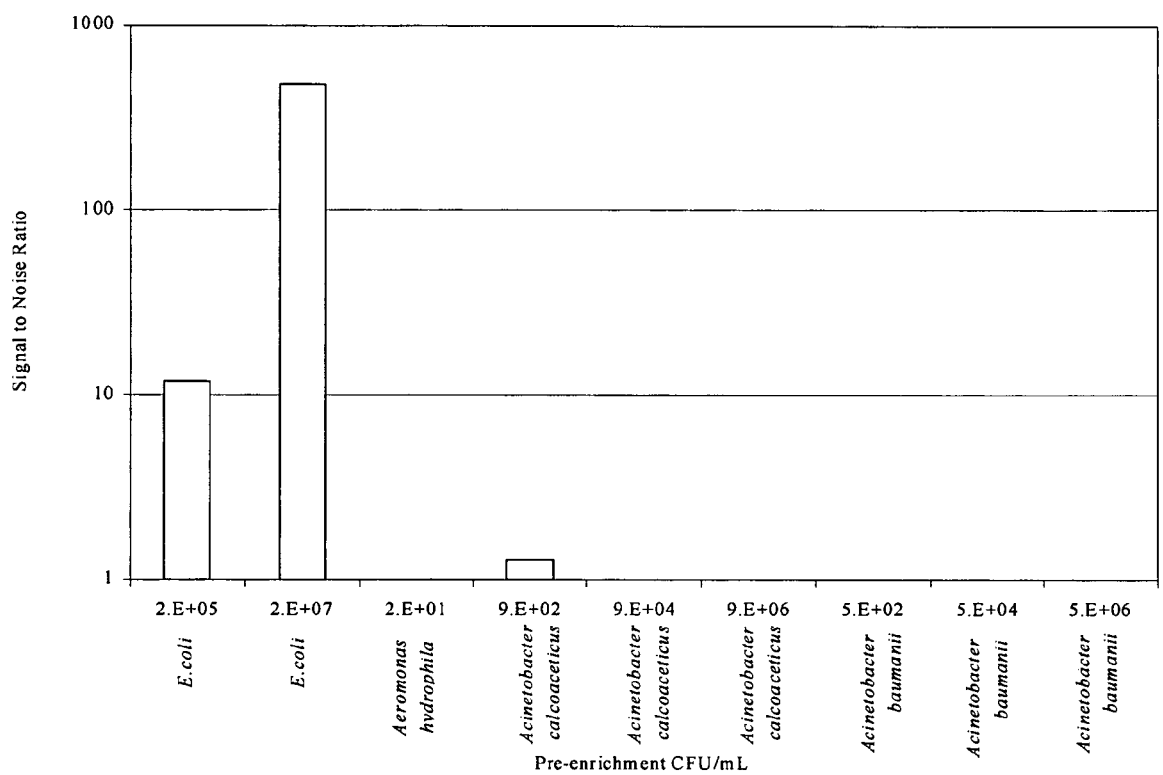
FIG. 3 shows the signal to noise ratio for false-positive non-target organisms and target organisms at a range of concentrations.

Pure cultures of the target organism *E. coli* and the false-positive non-target organisms *Aeromonas hydrophila* and *Acinetobacter* spp. were analyzed using the assay of the present invention. The concentrations tested for non-target organisms are at the upper end of the range of concentrations encountered in real water samples. The results are shown in FIG. 3.

Since pure cultures were analyzed, the signal to noise ratio indicates the contribution to the overall light reading of the organism present in the sample. The signal obtained from target organisms is much stronger than the signal from non-target organisms. In fact, for all non-target organisms but *Acinetobacter calcoaceticus*, the signal obtained was negligible. These results indicate that at typical environmental concentrations, the sensitivity of the assay is sufficient to reduce the likelihood of false-positive results due to the presence of non-target organisms in the water sample.

Example 4

A calibration curve with corresponding signal to noise ratio prepared using waters from a given source.

A water sample containing target organisms was diluted to obtain a number of samples over a range of concentrations. Each sample was split into aliquots and analyzed using the assay of the present invention and the membrane filtration (MF) technique. The results of the analyses are given in FIG. 4.

The MF results were plotted on the abscissa and the assay of the present invention on the ordinate axis. The corresponding signal to noise ratio was plotted on the secondary ordinate axis.

Since both target and non-target organisms were present, the signal to noise ratio indicates the signal obtained from the sample relative to the background light reading. A negative control (blank) is measured and the mean light reading on the luminometer provides the background noise level for subsequent tests. To determine the signal to noise ratio for a given sample, the water sample light reading (RLU) obtained from the sample is divided by the negative control light reading (RLU) previously obtained. A ratio greater than 2 is generally considered a positive response, indicating the presence of the target bacteria in the sample at a level discernable from the background noise level.

Figure 4:
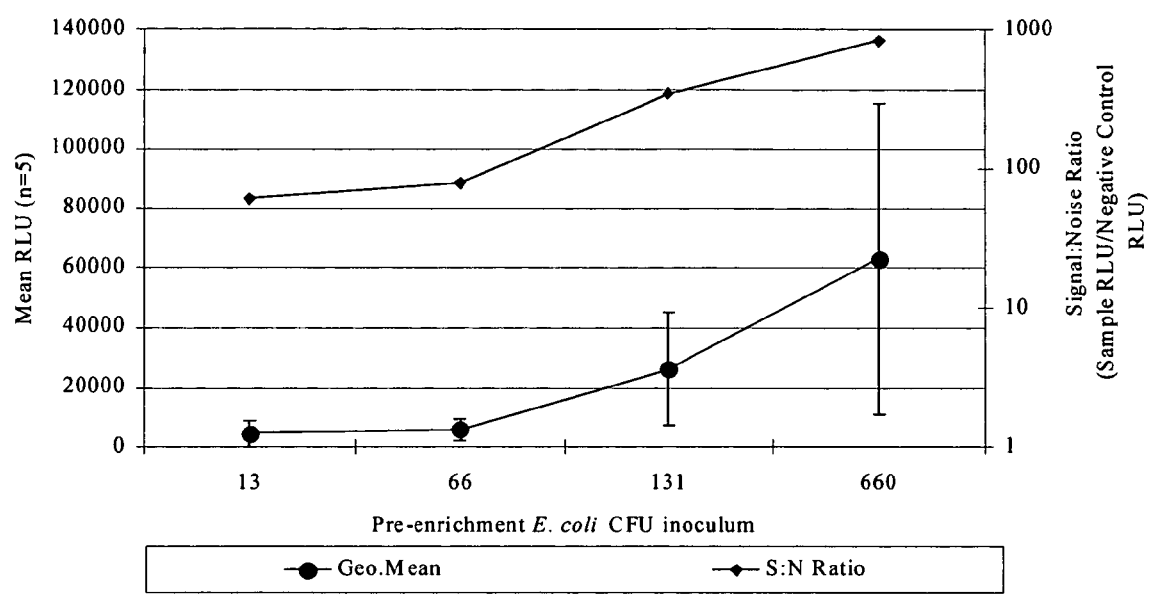
FIG. 4 shows a calibration curve prepared using waters from a given source.

With reference to FIG. 4, a correlation may be drawn between the quantity of bacteria in the sample obtained using the MF method and the corresponding light reading. To determine the quantity of bacteria in a sample, the mean RLU reading of the sample from the ordinate axis is cross referenced using the geometric mean of the MF results to determine the corresponding pre-enrichment *E. coli* CFU innoculum on the abscissa. The value thus obtained may be used for example as a semi-quantitative indication of the number of target bacteria in the sample or as a relative indication of the trend between samples. In practice, it may be useful to prepare fresh calibration curves periodically to account for variations in the background noise level of the source water being tested.

Example 5

Samples from a real water source were analyzed for total coliforms using the assay of the present invention and the results were compared with those obtained using the membrane filtration technique on mEndo media. Some of the samples were spiked with agricultural waste to increase the number of organisms available for detection. The results are presented in Table 1 below.

A positive result indicates the presence of more than 10 total coliforms per 100 mL sample, a level generally considered unsafe for drinking water. For the assay of the present invention, a signal to noise ratio greater than or equal to 2 was considered a positive result. By comparing the Test Result and Membrane Count columns, it can be seen that the assay generally produced a positive result when 10 or more coliforms were present in the sample and a negative result when less than 10 coliforms were present. In one sample, the signal to noise ratio indicated the presence of bacteria in the sample when the Membrane Count was 0. This was attributed to high background bacteria levels in the sample, which inhibit the growth of coliforms on mEndo media. In these instances of high background levels, coliforms that are present in the sample are not detected using colony counting methods such as the membrane filtration technique. The assay of the present invention may actually be more effective at indicating the presence of target bacteria in samples where high background levels interfere with colony counting assays. For the spiked samples, the signal to noise ratio was much greater than 2, regardless of whether the sample was from a drilled well or a tap water source. Table 1, inter alia, shows that the assay of the present invention is especially well suited to rapidly determining the microbiological safety of a drinking water supply.

From the foregoing, it will be seen that this invention is one well adapted to attain all the ends and objects hereinabove set forth together with other advantages which are obvious and which are inherent to the structure.

Since many possible embodiments may be made of the invention without departing from the scope thereof, it is to be understood that all matter herein set forth or shown in the accompanying examples is to be interpreted as illustrative and not in a limiting sense.

It will be understood that certain features and sub-combinations are of utility and may be employed without reference to other features and sub-combinations. This is contemplated by and is within the scope of the following claims.

TABLE 1

Data obtained using real water samples taken from a drilled well and a municipal tap water source.

| Sample Source | Spiking | Total Coliforms (RLU) | Total Coliforms (S:N) | Test Result (+/−) | Membrane Count (cfu/100 mL) | Notes |
| --- | --- | --- | --- | --- | --- | --- |
| Drilled Well | None | 3234 | 2.5 | + | 0 | High background |
| Drilled Well | None | 4677 | 1.4 | − | 0 | |
| Drilled Well | None | 3584 | 1.1 | − | 0 | |
| Drilled Well | Ag. waste | 418745 | 425.5 | + | 49 | |
| Drilled Well | Ag. waste | 154570 | 157.1 | + | 41 | |
| Drilled Well | Ag. waste | 64813 | 65.9 | + | 43 | |
| Drilled Well | Ag. waste | 24500 | 24.9 | + | 36 | |
| Drilled Well | Ag. waste | 40685 | 41.3 | + | 52 | |
| Drilled Well | Ag. waste | 45381 | 46.1 | + | 38 | |
| Drilled Well | Ag. waste | 42823 | 43.5 | + | 15 | |
| Tap Water | None | 1636.3 | 1.14 | − | 0 | |
| Tap Water | None | 1856 | 1.3 | − | 0 | |
| Tap Water | None | 1969 | 1.37 | − | 0 | |
| Tap Water | None | 1371.67 | 0.96 | − | 0 | |
| Tap Water | None | 1801.67 | 1.26 | − | 0 | |
| Tap Water | Ag.waste | 11488 | 14.5 | + | 17 | |
| Tap Water | Ag.waste | 9234 | 11.6 | + | 27 | |
| Tap Water | Ag.waste | 7697 | 9.7 | + | 21 | |
| Tap Water | Ag.waste | 11100 | 14.0 | + | 17 | |
| Tap Water | Ag.waste | 11195 | 14.1 | + | 21 | |
| Tap Water | Ag.waste | 24793 | 31.2 | + | 21 | |
| Tap Water | Ag.waste | 19352 | 24.4 | + | 22 | |
| Tap Water | Ag.waste | 11387 | 14.3 | + | 19 | |
| Tap Water | Ag.waste | 15473 | 19.5 | + | 29 | |
| Tap Water | Ag.waste | 1522 | 1.9 | + | 28 | |

The invention claimed is:

1. A method for determining the presence of coliform bacteria in a drinking water sample comprising the steps of:
   a) separating said bacteria from said drinking water sample using a first filter means;
   b) transferring said bacteria from said first filter means to a broth comprising nutrients for supporting growth of said bacteria and an inducing agent for inducing enzyme production in said bacteria and culturing said bacteria in said broth;
   c) separating said bacteria from said broth using a second filter means;
   d) exposing said bacteria to a lysing agent;
   e) incubating a chemiluminogenic substrate of said enzyme with said enzyme to cause cleavage of said substrate, thereby producing a luminescent product;
   f) initiating light emission by exposing said luminescent product to an enhancing agent that excludes water from a cleavage site of said substrate to prevent quenching of said light emission by water molecule induced protonation; and, g) detecting said light emission to thereby determine the presence of said bacteria in said sample.

2. The method of claim 1, wherein said bacteria are separated from said broth before being exposed to said lysing agent.

3. The method of claim 1, wherein said bacteria are on said second filter means during exposure to said lysing agent.

4. The method of claim 1, wherein said light emission is detected by means of a luminometer.

5. The method of claim 1, wherein said luminescent product is on said second filter means during detection of said light emission.

6. The method of claim 4, wherein said luminescent product is on said second filter means during detection of said light emission and wherein said second filter means is within said luminometer during detection of said light emission.

7. The method of claim 1, wherein said culturing is at a temperature of about 22 to 45° C. for about 2 to 10 hours.

8. The method of claim 1, wherein said chemiluminogenic substrate comprises 1,2-dioxetane.

9. The method of claim 1, wherein said enhancing agent comprises quaternary ammonium homopolymer.

10. The method of claim 1, wherein said enzyme is β-D-galactosidase.

11. The method of claim 10, wherein said culturing is at a temperature of about 35° C. for about 5 hours.

12. The method of claim 10, wherein said inducing agent comprises isopropyl-β-D-thiogalactopyranoside (IPTG), lactose, or a combination thereof.

13. The method of claim 10, wherein said substrate comprises 3-chloro-5-(4-methoxyspiro{1,2-dioxetane-3,2'-(5'-chloro)-tricyclo -[3.3.3.3$^{3,7}$]decan}-4-yl)phenyl β-D-galactopyranoside.

14. The method of claim 1, wherein said enzyme is β-D-glucuronidase.

15. The method of claim 14, wherein said culturing is at a temperature of about 44.5° C. for about 9 hours.

16. The method of claim 14, wherein said inducing agent comprises methyl-β-D-glucuronide (Met-Glu).

17. The method of claim 14, wherein said substrate comprises sodium 3-(4-methoxyspiro{1,2-dioxetane-3-, 2'-(5'-chloro)-tricyclo -[3.3.1.1$^{3,7}$]decan}-4-yl)phenyl β-D-glucuronate.

18. The method of claim 1, wherein said lysing agent is selected from toluene, successive freeze thaw cycles, a change of pressure, lysozyme, a detergent, octylphenoxypolyethoxyethanol nonionic surfactant, potassium dihydrogen phosphate, polymyxin-B, or a combination thereof.

19. The method of claim 1, wherein said broth further comprises an inhibiting agent for inhibiting the growth of non-target organisms.

20. A kit for determining the presence of coliform bacteria in a drinking water sample comprising:

a) a first filter means for separating said bacteria from said drinking water sample;

b) a broth comprising nutrients for supporting growth of said bacteria for use in culturing said bacteria after transferring said bacteria from said first filter means to said broth, said broth including an inducing agent comprising isopropyl-13-D-thiogalactopyranoside (IPTG) or methyl-13-D-glucuronide (Met-Glu) for inducing production of an enzyme in said bacteria;

c) a second filter means for separating said bacteria from said broth;

d) a lysing agent for exposure to said bacteria on said second filter means following separation;

e) a chemiluminogenic substrate of said enzyme for incubation with said enzyme to cause cleavage of said substrate, thereby producing a luminescent product on said second filter means;

f) an enhancing agent that excludes water from a cleavage site of said substrate to prevent quenching of said light emission by water molecule induced protonation, said enhancing agent for initiating light emission upon exposure to said luminescent product; and h) instructions for use of items a) to f) in accordance with their previously described functions.

* * * * *